(12) United States Patent
Kiyose

(10) Patent No.: US 10,074,795 B2
(45) Date of Patent: Sep. 11, 2018

(54) ULTRASONIC PROBE AS WELL AS ELECTRONIC APPARATUS AND ULTRASONIC IMAGING APPARATUS

(71) Applicant: SEIKO EPSON CORPORATION, Tokyo (JP)

(72) Inventor: Kanechika Kiyose, Nagano (JP)

(73) Assignee: Seiko Epson Corporation, Tokyo (JP)

( * ) Notice: Subject to any disclaimer, the term of this patent is extended or adjusted under 35 U.S.C. 154(b) by 475 days.

(21) Appl. No.: 14/920,272

(22) Filed: Oct. 22, 2015

(65) Prior Publication Data

US 2016/0126445 A1    May 5, 2016

(30) Foreign Application Priority Data

Oct. 31, 2014    (JP) .................. 2014-222470

(51) Int. Cl.

| | | |
|---|---|---|
| H01L 41/09 | (2006.01) | |
| H01L 41/113 | (2006.01) | |
| H01L 41/053 | (2006.01) | |
| A61B 8/00 | (2006.01) | |

(52) U.S. Cl.
CPC ........ *H01L 41/0533* (2013.01); *A61B 8/4427* (2013.01); *A61B 8/4455* (2013.01); *A61B 8/4483* (2013.01)

(58) Field of Classification Search
CPC .......................... H01L 41/0533; A61B 8/4427

USPC ................. 310/317, 318, 319, 322, 324, 334
See application file for complete search history.

(56) References Cited

U.S. PATENT DOCUMENTS

| | | | | |
|---|---|---|---|---|
| 4,771,205 A | * | 9/1988 | Mequio .................. | G10K 11/02 310/327 |
| 5,297,553 A | * | 3/1994 | Sliwa, Jr. .............. | B06B 1/0674 29/25.35 |
| 5,792,058 A | * | 8/1998 | Lee ........................ | B06B 1/0622 600/459 |
| 6,492,762 B1 | * | 12/2002 | Pant ...................... | B06B 1/0688 310/334 |
| 2008/0243001 A1 | * | 10/2008 | Oakley ................ | A61B 8/4281 600/459 |

FOREIGN PATENT DOCUMENTS

| | | |
|---|---|---|
| JP | 2002-199494 A | 7/2002 |
| JP | 2003-017838 A | 1/2003 |

\* cited by examiner

*Primary Examiner* — Thomas Dougherty

(57) ABSTRACT

An ultrasonic probe is provided that makes it possible to increase the shock resistance of a board of an ultrasonic device unit. An ultrasonic probe includes a housing. The housing defines an opening and an accommodation space that is continuous with the opening. An ultrasonic device unit is disposed in the accommodation space. A board has on its first surface an ultrasonic transducer that faces the opening. A rigid body is in contact with a second surface of the board and the housing. The rigid body has higher stiffness than the board.

9 Claims, 9 Drawing Sheets

ULTRASONIC PROBE AS WELL AS ELECTRONIC APPARATUS AND ULTRASONIC IMAGING APPARATUS

BACKGROUND

1. Technical Field

The present invention relates to an ultrasonic probe as well as an electronic apparatus, an ultrasonic imaging apparatus, and the like using the ultrasonic probe.

2. Related Art

JP-A-2002-199494 discloses an ultrasonic probe. In the ultrasonic probe, a cable board and an oscillator unit are accommodated in a hollow portion of a housing. Comb-like lead terminals are formed on a surface of the cable board. Electrodes of the oscillator unit are joined to the lead terminals. The inside of the hollow portion is filled with an adhesive composed of an insulating resin material. The adhesive ensures insulation between the lead terminals and between the electrodes.

JP-A-2002-199494 mentions the insulating property of the adhesive, but makes no mention of the stiffness of the adhesive. Even if the adhesive is in contact with the cable board, deformation of the cable board is unavoidable if the adhesive has greater elasticity than the cable board. It is feared that the cable board may be damaged.

SUMMARY

According to at least one aspect of the invention, an ultrasonic probe can be provided that makes it possible to increase the shock resistance of a board of an ultrasonic device unit.

(1) An aspect of the invention is directed to an ultrasonic probe including a housing that defines an opening and an accommodation space that is continuous with the opening, an ultrasonic device unit that is disposed in the accommodation space and that has a board including on a first surface thereof an ultrasonic transducer that faces the opening, and a rigid body that is in contact with a second surface of the board, the second surface being on a side opposite to the first surface, and the housing and that has higher stiffness than the board.

The ultrasonic transducer receives ultrasonic waves reflected by a target. Even when an external shock is applied to the housing, the board of the ultrasonic device unit is kept from deforming because the rigid body is in contact with the board. Thus, the stress in the board is dispersed to the rigid body, and therefore the board can be prevented from being damaged. The shock resistance of the ultrasonic probe can be increased.

(2) It is possible that in a plan view as seen in a thickness direction of the board, the rigid body has a size that covers a region in which the ultrasonic transducer is disposed. Thus, in the region in which the ultrasonic element is disposed, the rigid body reinforces the stiffness of the board. The board is kept from deforming.

(3) It is sufficient if the rigid body is disposed outside a region containing an external connection terminal portion to which a wire is connected on the second surface of the board. When a conducting line of the wire is connected to the external connection terminal portion, the stiffness of the board in the region containing the external connection terminal portion is reinforced. If the rigid body is disposed outside the region containing the external connection terminal portion, the stiffness of the board is reinforced also in a region outside the region containing the external connection terminal portion. Thus, the board is kept from deforming.

(4) It is sufficient if, in a plan view as seen in the thickness direction of the board, the rigid body is disposed outside an outline of a connector that is mounted on the second surface of the board. When the connector is mounted on the board, the stiffness of the board in a region that is defined by the outline of the connector is reinforced. If the rigid body is disposed outside the outline of the connector, the stiffness of the board is reinforced also in a region outside the outline of the connector. Thus, the board is kept from deforming. Furthermore, if the rigid body is disposed so as not to overlap the region of the connector, the attachment/detachment of the connector is ensured even if the rigid body is coupled to the board.

(5) It is possible that the ultrasonic probe further includes an elastic body that is disposed on a back side of the ultrasonic transducer outside an outline of the rigid body in a plan view as seen in the thickness direction of the board and that has a smaller modulus of elasticity than the board. Even when the elastic body comes into contact with the board, displacement of the board is accommodated in accordance with deformation of the elastic body. Thus the attachment accuracy required with respect to the board is alleviated.

(6) It is preferable that the elastic body is sandwiched between the connector and the housing. The elastic body presses the connector against the board. As a result, unintentional detachment of the connector can be prevented. Furthermore, since displacement of the connector is accommodated in accordance with the deformation of the elastic body, the positioning accuracy required with respect to the connector is alleviated.

(7) It is sufficient if the rigid body and the elastic body are formed of a resin material. The rigid body and the elastic body may be formed as a single resin body. The rigid body and the elastic body can be easily processed. If the rigid body and the elastic body are integrated into a single body, the operation of assembling the rigid body and the elastic body is simplified.

(8) It is possible that with respect to the rigid body, a filler is mixed in a base material of the resin material. The stiffness of the resin material is adjusted in accordance with the mixing of the filler. The filler can buffer ultrasonic waves that come from the ultrasonic transducer to a rear side thereof. Thus, the influence of reflected waves from the resin material toward the ultrasonic transducer is avoided.

(9) The ultrasonic probe can be used as one component of an electronic apparatus. At this time, it is sufficient if the electronic apparatus includes the ultrasonic probe and a processing unit that is connected to the ultrasonic device unit and that processes an output from the ultrasonic device unit.

(10) The ultrasonic probe can be used as one component of an ultrasonic imaging apparatus. At this time, it is sufficient if the ultrasonic imaging apparatus includes the ultrasonic probe, a processing unit that is connected to the ultrasonic device unit and that processes an output from the ultrasonic device unit and generates an image, and a display device that displays the image.

BRIEF DESCRIPTION OF THE DRAWINGS

The invention will be described with reference to the accompanying drawings, wherein like numbers reference like elements.

DESCRIPTION OF EXEMPLARY EMBODIMENTS

The following describes embodiments of the invention with reference to the attached drawings. It should be noted that the embodiments to be described hereinafter are not intended to unduly limit the scope of the invention defined by the claims and that not all of the configurations to be described in the embodiments are necessarily essential as the means for achieving the invention.

(1) Overall Configuration of Ultrasonic Diagnostic Apparatus

Figure 1:
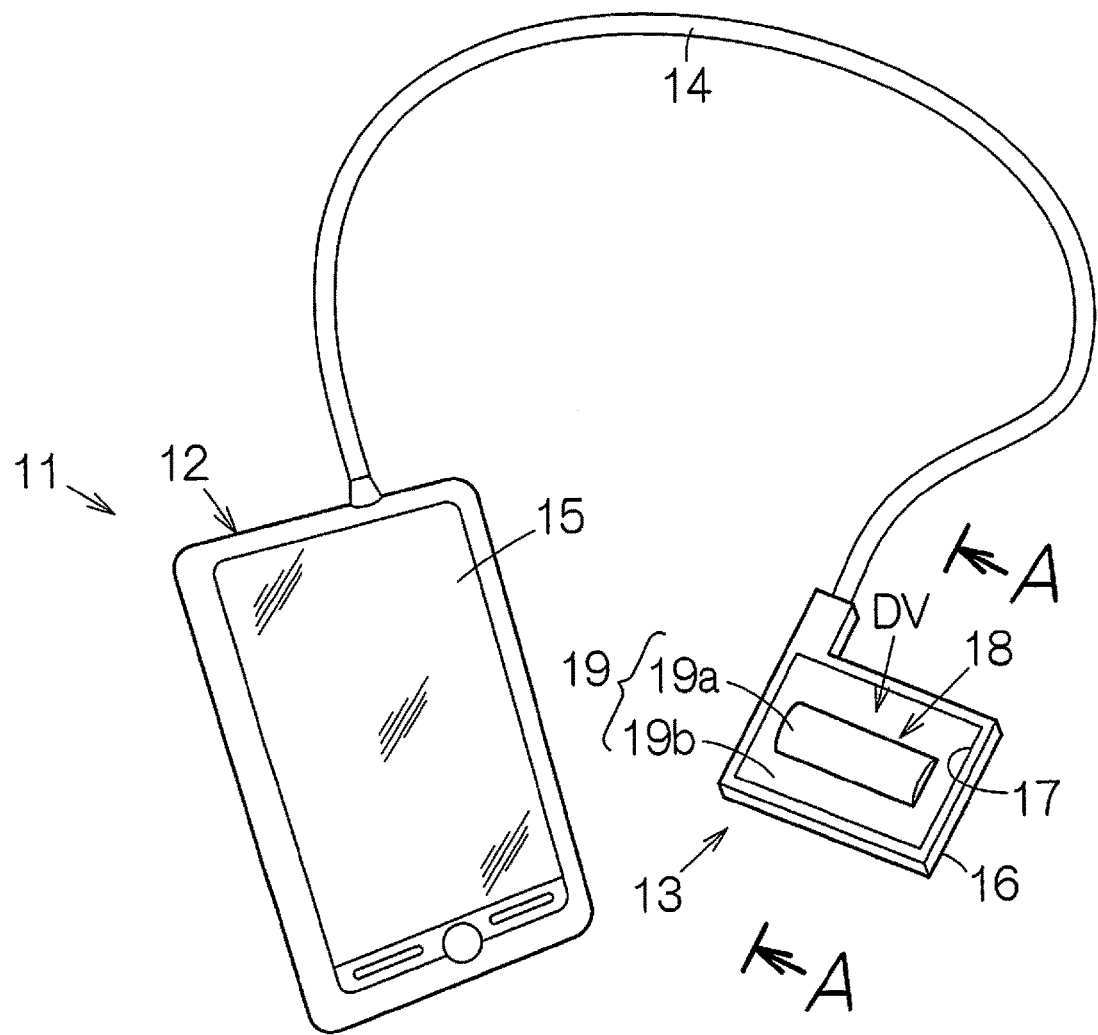
FIG. 1 is an external view schematically showing a specific example, that is, an ultrasonic diagnostic apparatus, of an electronic apparatus according to an embodiment.

FIG. 1 schematically shows the configuration of a specific example, that is, an ultrasonic diagnostic apparatus (ultrasonic imaging apparatus) 11, of an electronic apparatus according to an embodiment of the invention. The ultrasonic diagnostic apparatus 11 includes a device terminal (processing unit) 12 and an ultrasonic probe (probe) 13. The device terminal 12 and the ultrasonic probe 13 are connected to each other via a cable 14. Electric signals are transmitted through the cable 14 between the device terminal 12 and the ultrasonic probe 13. A display panel (display device) 15 is incorporated into the device terminal 12. A screen of the display panel 15 is exposed at a surface of the device terminal 12. In the device terminal 12, an image is generated based on ultrasonic waves detected by the ultrasonic probe 13. The imaged detection result is displayed on the screen of the display panel 15.

(2) Configuration of Ultrasonic Probe According to First Embodiment

The ultrasonic probe 13 has a housing 16. An ultrasonic device unit DV is fitted in the housing 16. An opening 17 is formed in the housing 16. The opening 17 faces an accommodation space that is defined in the housing 16. The ultrasonic device unit DV is disposed in the accommodation space.

The ultrasonic device unit DV includes an ultrasonic device 18. The ultrasonic device 18 includes an acoustic lens 19. A partial cylindrical surface 19a is formed on an outer surface of the acoustic lens 19. The partial cylindrical surface 19a is surrounded by a flat plate portion 19b. The entire outer perimeter of the flat plate portion 19b is continuously coupled to the housing 16. Thus, the flat plate portion 19b functions as a portion of the housing. The acoustic lens 19 may be formed of a silicone resin, for example. The acoustic lens 19 has an acoustic impedance that is similar to the acoustic impedance of a living body. The ultrasonic device 18 outputs ultrasonic waves from its surface and receives reflected waves of the ultrasonic waves.

Figure 2:
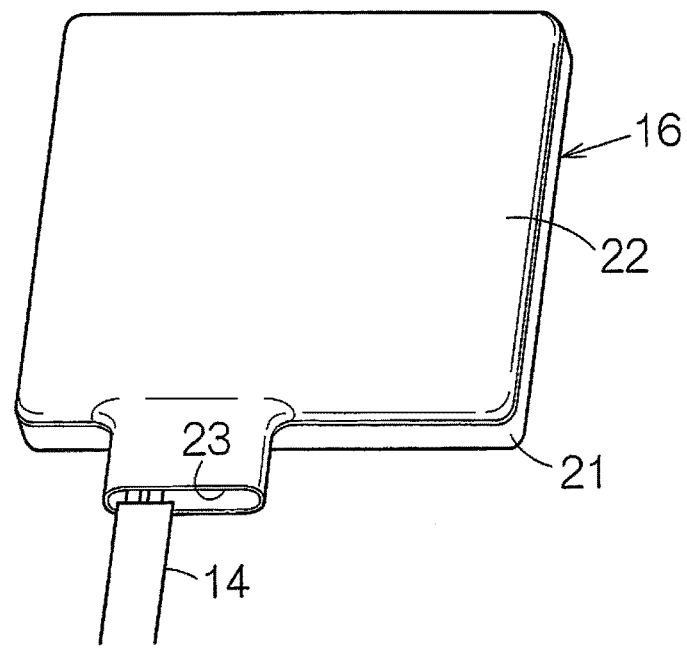
FIG. 2 is an enlarged rear view of an ultrasonic probe.

FIG. 2 shows a rear surface (back surface) of the ultrasonic probe 13. As shown in FIG. 2, the housing 16 includes a front-side frame 21 and a back-side body 22. The front-side frame 21 and the back-side body 22 are coupled to each other. In a region between the front-side frame 21 and the back-side body 22, a cable port 23 is defined between a coupling surface of the front-side frame 21 and a coupling surface of the back-side body 22. The cable 14 is disposed in the cable port 23.

Figure 3:
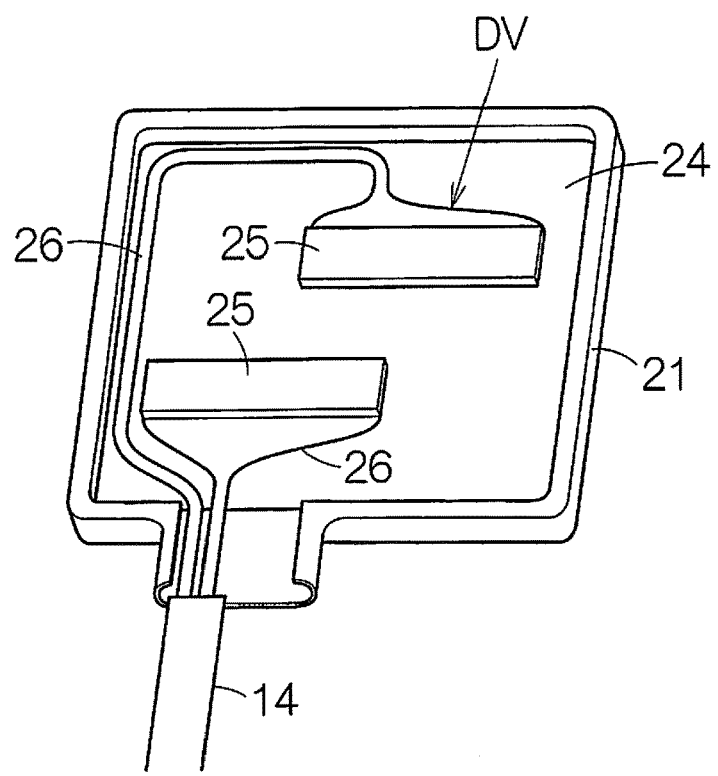
FIG. 3 is a rear view schematically showing a front-side frame and an ultrasonic device unit of the ultrasonic probe.

As shown in FIG. 3, the ultrasonic device unit DV is fitted in the front-side frame 21. The ultrasonic device unit DV includes a circuit board 24. The ultrasonic device 18 is fixed to the front side of the circuit board 24 as described later. Connectors 25 are mounted on the back side of the circuit board 24.

Wires 26 are coupled to the individual connectors 25. To couple the wires 26 thereto, a male connector is connected to a leading end of each wire 26. The male connectors of the wires 26 are received by the corresponding connectors 25, that is, female connectors on the circuit board 24. These wires 26 are bundled together, and the bundle of the wires 26 forms the cable 14.

Figure 4:
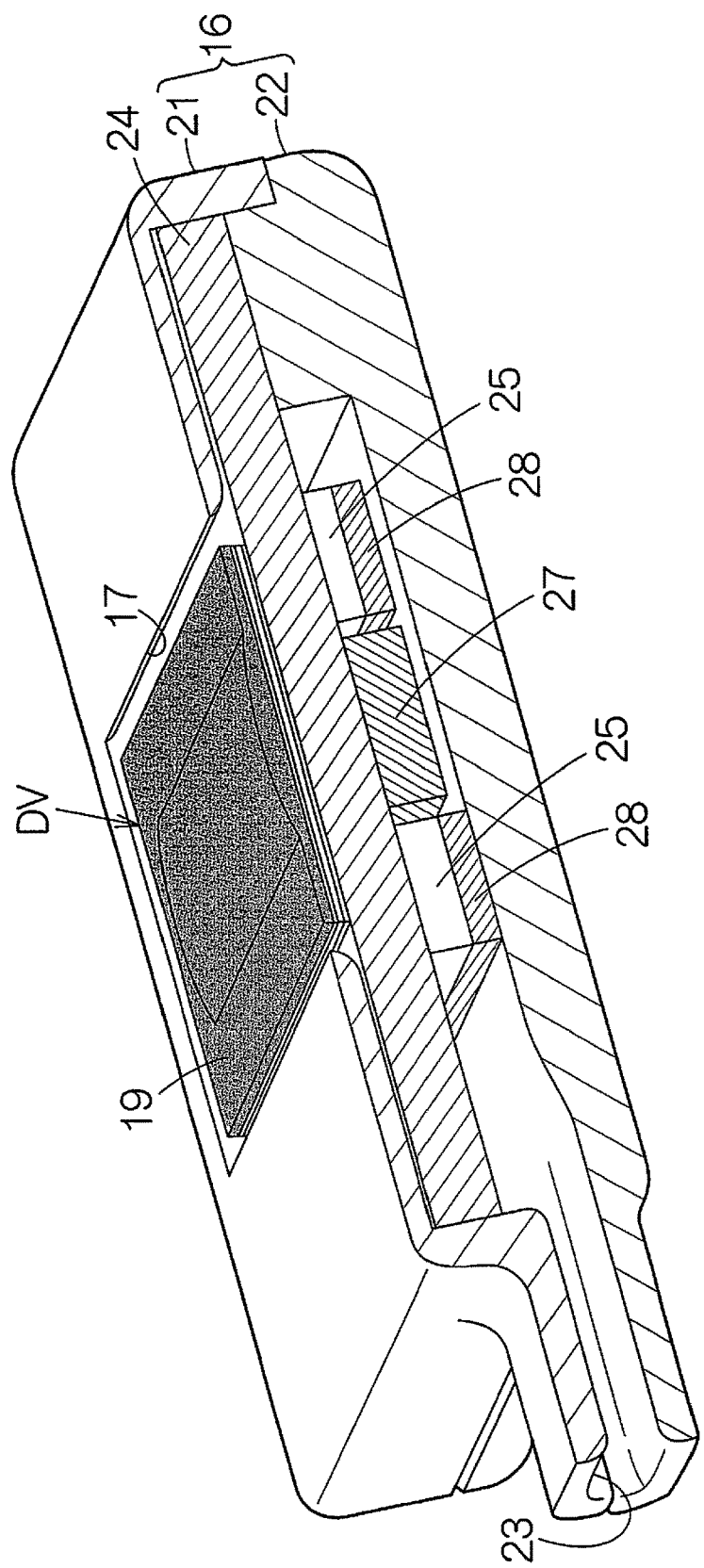
FIG. 4 is a cross-sectional view taken along line A-A in FIG. 1.

As shown in FIG. 4, a rigid body 27 is disposed in the housing 16. The rigid body 27 is fixed to the back-side body 22. The rigid body 27 has higher stiffness than the circuit board 24, for example. The stiffness can be calculated based on the Young's modulus, for example. The higher the stiffness of an object is, the less the object is likely to deform.

Elastic bodies 28 are disposed in the housing 16. The elastic bodies 28 are fixed to the back-side body 22. The elastic bodies 28 have greater elasticity than the circuit board 24, for example. The elasticity can be calculated based on the Young's modulus, for example. The greater the elasticity of an object is, the more the object is likely to elastically deform. For example, cushion tape can be used as the elastic bodies 28.

(3) Configuration of Ultrasonic Device

Figure 5:
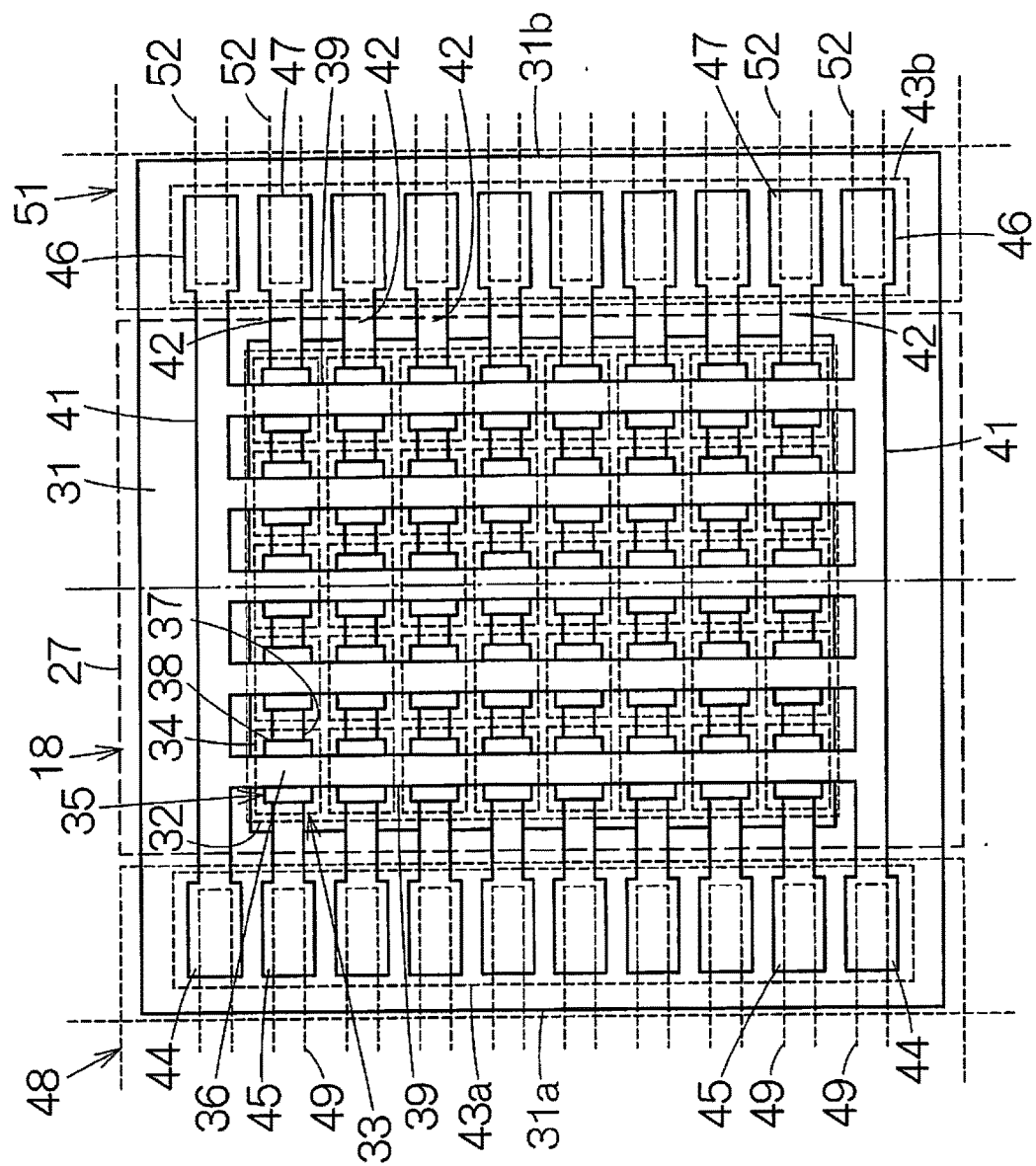
FIG. 5 is an enlarged plan view of an ultrasonic device according to an embodiment.

FIG. 5 schematically shows a plan view of the ultrasonic device 18. The ultrasonic device 18 includes a base 31. An element array 32 is formed on a surface of the base 31. The element array 32 is constituted by an arrangement of thin-film ultrasonic transducer elements (hereinafter referred to as "elements") 33 that are arranged in an array. The arrangement is in the form of a matrix having a plurality of columns and a plurality of rows. The arrangement may also be established as a staggered arrangement. In a staggered arrangement, a group of elements 33 in even rows can be displaced relative to a group of elements 33 in odd rows by one-half of the column pitch. One of the number of elements in a single odd row and the number of elements in a single even row may be smaller than the other by one. Here, the rigid body 27 has a size that covers the element array 32 in a plan view as seen in a thickness direction of the base 31.

Each element 33 includes a vibration film 34. In FIG. 5, the outline of the vibration film 34 in a plan view as seen in a direction perpendicular to the film surface of the vibration film 34 (in a plan view as seen in a thickness direction of a board) is shown by dashed lines. A piezoelectric element 35 is formed on the vibration film 34. The piezoelectric element 35 is composed of a top electrode 36, a bottom electrode 37, and a piezoelectric film 38. For each element 33, the piezoelectric film 38 is sandwiched between the top electrode 36 and the bottom electrode 37. The bottom electrode 37, the piezoelectric film 38, and the top electrode 36 are laid one on top of another in that order. The ultrasonic device 18 is configured as a single ultrasonic transducer element chip (board).

A plurality of first electric conductors 39 are formed on the surface of the base 31. The first electric conductors 39 extend parallel to one another in a column direction of the arrangement. One first electric conductor 39 is assigned to corresponding one column of elements 33. One first electric conductor 39 is connected in common to the piezoelectric films 38 of the respective elements 33 that are lined up in the column direction of the arrangement. The first electric conductor 39 forms the top electrodes 36 for the individual elements 33. Both ends of the first electric conductor 39 are connected to a pair of extraction interconnects 41. The extraction interconnects 41 extend parallel to each other in a row direction of the arrangement. Accordingly, all of the first electric conductors 39 have the same length. Thus, the top electrodes 36 are connected in common to the elements 33 of the entire matrix. The first electric conductors 39 can be formed of iridium (Ir), for example. However, other electrically conductive materials may also be used for the first electric conductors 39.

A plurality of second electric conductors 42 are formed on the surface of the base 31. The second electric conductors 42 extend parallel to one another in the row direction of the arrangement. One second electric conductor 42 is assigned to corresponding one row of elements 33. One second electric conductor 42 is connected in common to the piezoelectric films 38 of the respective elements 33 that are lined up in the row direction of the arrangement. The second electric conductor 42 forms the bottom electrodes 37 for the individual elements 33. For example, a laminated film composed of titanium (Ti), iridium (Ir), platinum (Pt), and titanium (Ti) can be used for the second electric conductors 42. However, other electrically conductive materials may also be used for the second electric conductors 42.

Energization of the elements 33 is switched on a row-by-row basis. A linear scan and a sector scan can be achieved in accordance with this switching of energization. Since the elements 33 in a single row simultaneously output ultrasonic waves, the number of elements in a single row, that is, the number of columns of the arrangement can be determined in accordance with the output level of ultrasonic waves. The number of columns can be set at about 10 to 15, for example. In FIG. 5, some columns are not shown, and only five columns are shown. The number of rows of the arrangement can be determined in accordance with the extent of the scan range. The number of rows can be set at 128 or 256, for example. In FIG. 5, some rows are not shown, and only eight rows are shown. The functions of the top electrodes 36 and the bottom electrodes 37 may be reversed. That is to say, it is also possible that while the bottom electrodes are connected in common to the elements 33 of the entire matrix, the top electrodes are connected in common to the elements 33 in each row of the arrangement.

The outline of the base 31 has a first side 31a and a second side 31b that are defined by a pair of mutually parallel straight lines and that oppose each other. A first terminal array 43a in a single line is disposed between the first side 31a and the outline of the element array 32. A second terminal array 43b in a single line is disposed between the second side 31b and the outline of the element array 32. The first terminal array 43a can form a single line parallel to the first side 31a. The second terminal array 43b can form a single line parallel to the second side 31b. The first terminal array 43a is constituted by a pair of top electrode terminals 44 and a plurality of bottom electrode terminals 45. Similarly, the second terminal array 43b is constituted by a pair of top electrode terminals 46 and a plurality of bottom electrode terminals 47. One top electrode terminal 44 and one top electrode terminal 46 are respectively connected to the two ends of a single extraction interconnect 41. It is sufficient if the extraction interconnects 41 and the top electrode terminals 44 and 46 are formed plane-symmetrically with respect to a perpendicular plane that bisects the element array 32. One bottom electrode terminal 45 and one bottom electrode terminal 47 are respectively connected to the two ends of a single second electric conductor 42. It is sufficient if the second electric conductors 42 and the bottom electrode terminals 45 and 47 are formed plane-symmetrically with respect to a perpendicular plane that bisects the element array 32. Here, the base 31 is formed to have a rectangular outline. The outline of the base 31 may also be square or may be trapezoidal.

A first flexible printed wiring board (hereinafter referred to as "first wiring board") 48 is connected to the base 31. The first wiring board 48 covers the first terminal array 43a. Electrically conductive lines, namely, first signal lines 49 are formed at one end of the first wiring board 48, individually corresponding to the top electrode terminals 44 and the bottom electrode terminals 45. The first signal lines 49 are individually opposed to the top electrode terminals 44 and the bottom electrode terminals 45 and individually joined thereto. Similarly, a second flexible printed wiring board (hereinafter referred to as "second wiring board") 51 covers the base 31. The second wiring board 51 covers the second terminal array 43b. Electrically conductive lines, namely, second signal lines 52 are formed at one end of the second wiring board 51, individually corresponding to the top electrode terminals 46 and the bottom electrode terminals 47. The second signal lines 52 are individually opposed to the top electrode terminals 46 and the bottom electrode terminals 47 and individually joined thereto.

Figure 6:
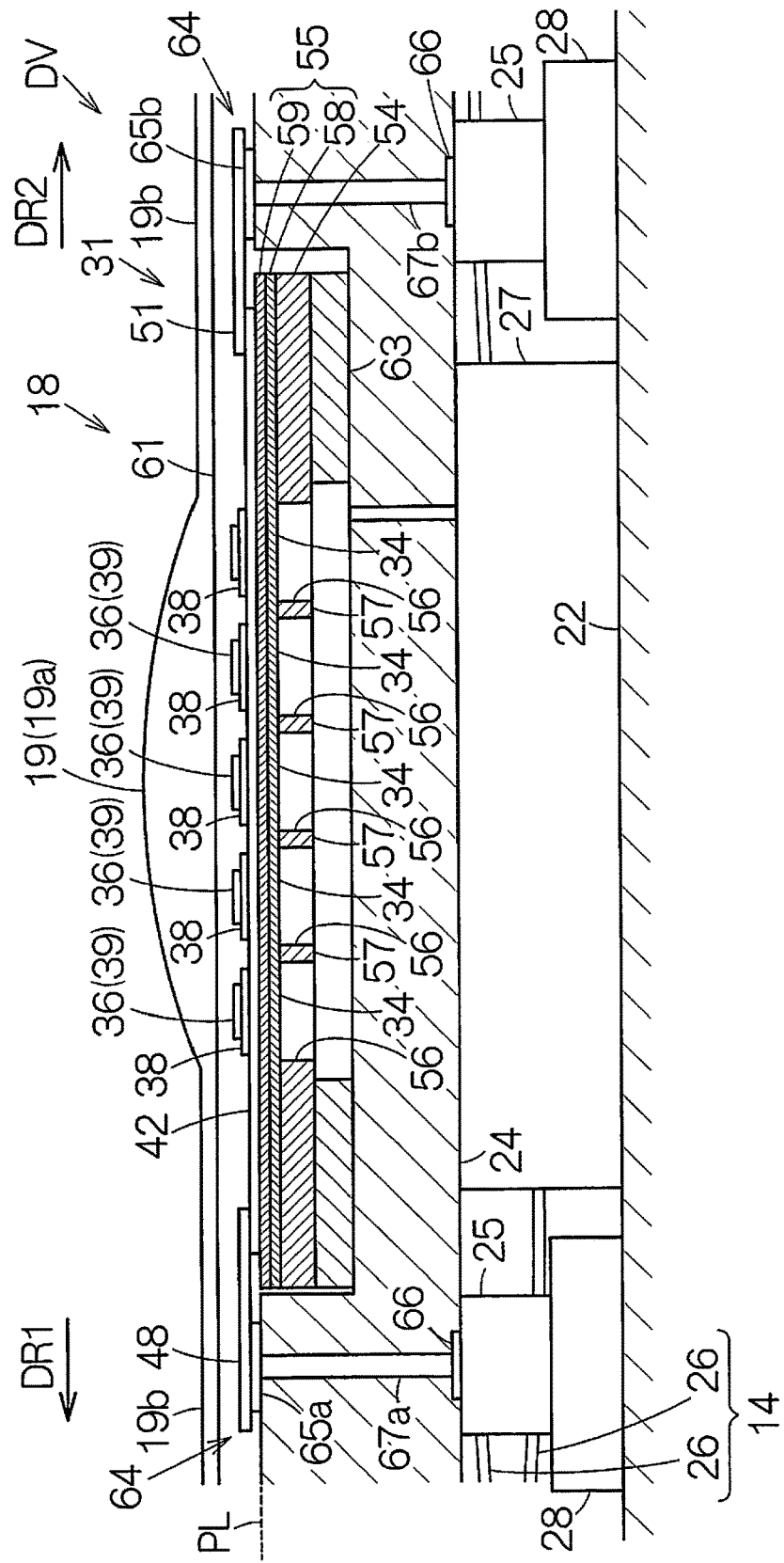
FIG. 6 is a partial cross-sectional view, taken along line A-A in FIG. 1, of the ultrasonic device according to the embodiment.

As shown in FIG. 6, the base 31 includes a substrate 54 and a coating film 55. The coating film 55 is formed over the entire surface of the substrate 54. In the substrate 54, an opening 56 is formed for each element 33. The openings 56 are arranged in an array in the substrate 54. The opening 56 for each element 33 opens in a surface on the back side (opposite side). The outline of a region where the openings 56 are arranged corresponds to the outline of the element array 32. A partitioning wall 57 is disposed between every two adjacent openings 56. Adjacent openings 56 are separated from each other by the partitioning walls 57. The wall thickness of the partitioning walls 57 corresponds to the spacing between the openings 56. The substrate 54 can be formed of a silicon substrate, for example.

The coating film 55 is composed of a silicon oxide ($SiO_2$) layer 58 that is laminated on a surface of the substrate 54 and a zirconium oxide ($ZrO_2$) layer 59 that is laminated on a surface of the silicon oxide layer 58. The coating film 55 closes the spaces of the openings 56. Thus, a portion of the coating film 55 forms the vibration film 34 corresponding to the outline of each opening 56. The vibration films 34 refer to those portions of the coating film 55 that face the respective openings 56 and that can thus vibrate in the thickness direction of the substrate 54. The film thickness of the silicon oxide layer 58 can be determined based on the resonance frequency.

The bottom electrode 37, the piezoelectric film 38, and the top electrode 36 are sequentially laminated on the surface of each vibration film 34. The piezoelectric film 38 can be formed of lead zirconate titanate (PZT), for example. Other piezoelectric materials may also be used for the piezoelectric film 38. Here, the piezoelectric film 38 completely covers the corresponding second electric conductor 42 underneath the first electric conductor 39. The piezoelectric film 38 can serve to avoid short-circuiting between the first electric conductor 39 and the second electric conductor 42.

An acoustic matching layer 61 is laminated on the surface of the base 31. The acoustic matching layer 61 covers the element array 32. The film thickness of the acoustic matching layer 61 is determined based on the resonance frequency of the vibration films 34. For example, a silicone resin film can be used for the acoustic matching layer 61. The acoustic lens 19 is disposed on the acoustic matching layer 61. A flat surface of the acoustic lens 19 that is on the back side of the partial cylindrical surface 19a is in close contact with a surface of the acoustic matching layer 61. The acoustic lens 19 is bonded to the base 31 by the function of the acoustic matching layer 61. The generating lines of the partial cylindrical surface 19a are positioned parallel to the first electric conductors 39. The curvature of the partial cylindrical surface 19a is determined in accordance with the focus position of ultrasonic waves emitted from a single row of elements 33 connected to a single second electric conductor 42.

A reinforcing plate 63 serving as a backing material is coupled to the back surface of the base 31. The reinforcing plate 63 is formed into a flat plate shape. The back surface of the base 31 is laid on top of a surface of the reinforcing plate 63. The surface of the reinforcing plate 63 is joined to the back surface of the base 31. At this time, the reinforcing plate 63 may be bonded to the base 31 with an adhesive. The reinforcing plate 63 reinforces the stiffness of the base 31. The reinforcing plate 63 serves to secure favorable flatness of the surface of the base 31. The reinforcing plate 63 can include a rigid base material, for example. This base material can be formed of a metal material such as Alloy 42 (iron-nickel alloy), for example.

Wiring patterns 64 are formed on the circuit board 24. The first wiring board 48 and the second wiring board 51 of the ultrasonic device 18 are connected to the corresponding wiring patterns 64. The wiring patterns 64 include first electrically conductive pads 65a and second electrically conductive pads 65b. The first electrically conductive pads 65a and the second electrically conductive pads 65b are formed on a plane PL of the circuit board 24. The first electrically conductive pads 65a and the second electrically conductive pads 65b are arranged so as to correspond to the first signal lines 49 and the second signal lines 52. The first electrically conductive pads 65a and the second electrically conductive pads 65b can be formed of an electrically conductive material such as copper, for example. The first electrically conductive pads 65a and the second electrically conductive pads 65b are joined to the corresponding first signal lines 49 and second signal lines 52.

One end of the first wiring board 48 is laid on top of and connected to the ultrasonic device 18 at a position higher than the plane PL of the circuit board 24. The first wiring board 48 extends in a first direction DR1 from this end that is located on the ultrasonic device 18. The other end of the first wiring board 48 is laid on top of and connected to the plane PL of the circuit board 24. Similarly, one end of the second wiring board 51 is laid on top of and connected to the ultrasonic device 18 at a position higher than the plane PL of the circuit board 24. The second wiring board 51 extends in a second direction DR2 from this end that is located on the ultrasonic device 18. The second direction DR2 is opposite to the first direction DR1. The other end of the second wiring board 51 is laid on top of and connected to the plane PL of the circuit board 24.

The wiring patterns 64 have external connection terminals 66 that are formed on the back surface of the circuit board 24. The connectors 25 are mounted to the external connection terminals 66. One of the connectors 25 is connected to the first electrically conductive pads 65a through vias 67a. The other connector 25 is connected to the second electrically conductive pads 65b through vias 67b. The vias 67a and 67b pass through the circuit board 24 from the surface to the back surface thereof. As is clear from FIG. 6, the rigid body 27 is disposed outside the outlines of the connectors 25 in a plan view perpendicular to the back surface of the circuit board 24. The rigid body 27 is in contact with the circuit board 24 on the back side of the elements 33. Similarly, the elastic bodies 28 are individually in contact with the corresponding connectors 25 on the back side of the elements 33. The elastic bodies 28 are disposed outside the outline of the rigid body 27 in a plan view as seen in the thickness direction of the circuit board 24.

Figure 7:
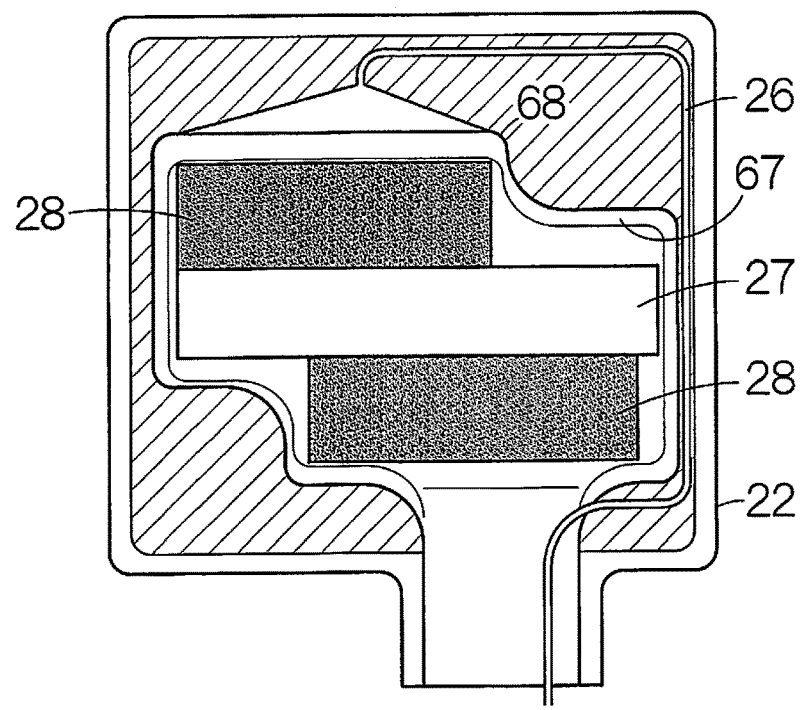
FIG. 7 is an enlarged plan view schematically showing the structure of a back-side body.

Here, as shown in FIG. 7, to install the rigid body 27 and the elastic bodies 28, a recess 67 is formed in the back-side body 22 of the housing 16. A ridge 68 is formed along the outline of the recess 67. The ridge 68 together with the curves and bends in the outline of the recess 67 serves to increase the stiffness of the flat plate-shaped back-side body 22. Thus, at least on the back side of the circuit board 24, the housing 16 has higher stiffness than the circuit board 24. In addition, the housing 16 may have higher stiffness than the circuit board 24 depending on the material for the housing 16. Similarly to the rigid body 27, the housing 16 may be formed of a carbon fiber reinforced plastic (CFRP). More preferably, it is ensured that the back-side body 22 has a large thickness in a region outside the recess 67 because if so, the housing 16 can have higher stiffness than the circuit board 24.

To evaluate the stiffness, a three-point bending test apparatus (JIS K7171:2008), for example, may be used. Here, the bending load when a test target was bent by 0.5 mm under the conditions of a distance between support points of 15 [mm] and a head speed of 1 [mm/min] was used for evaluation of the stiffness. For example, it is assumed that a 26 mm (long axis direction of the element array 32)×10 mm (short axis direction of the element array 32)×2.1 mm (thickness) rigid body 27 is fitted to a 26 mm (long axis direction of the element array 32)×24 mm (short axis direction of the element array 32)×1.6 mm (thickness) glass epoxy substrate (Young's modulus: 23 GPa). Since the stiffness is proportional to the product of the moment of inertia of area in the long axis direction and the Young's modulus, if a Young's modulus of 32 GPa or more is imparted to the rigid body 27, the rigid body 27 can have higher stiffness than the circuit board 24. Examples of the material having such a Young's modulus include stainless steel, aluminum, a magnesium alloy, a carbon fiber reinforced plastic (CFRP), and the like.

To evaluate the elasticity, a compression test (JIS K7181: 2010), for example, may be used. Here, the modulus of compressive elasticity is measured. The elasticity is evaluated based on the Young's modulus, which is a type of modulus of elasticity. For example, most resin materials such as an ABS resin, a PP resin, a PC resin, and others have a smaller modulus of compressive elasticity than glass epoxy. Preferably, a silicone resin, an urethane resin, an elastomer, and the like may be used.

As shown in FIG. 7, the wires 26 are disposed outside the outline of the rigid body 27 in a plan view. The wires 26 do not overlap the rigid body 27. Furthermore, the wires 26 are located outside the elastic bodies 28. As shown in FIG. 3, the wires 26 may be fixed to the back side of the circuit board 24 so that the wires 26 are located in such an arrangement.

(4) Operation of Ultrasonic Diagnostic Apparatus

Next, the operation of the ultrasonic diagnostic apparatus 11 will be briefly described. To transmit ultrasonic waves, a pulse signal is supplied to the piezoelectric elements 35. The pulse signal is supplied to the elements 33 on a row-by-row basis through the bottom electrode terminals 45 and 47 and the top electrode terminals 44 and 46. In each element 33, an electric field acts on the piezoelectric film 38 between the bottom electrode 37 and the top electrode 36. The piezoelectric film 38 vibrates at an ultrasonic frequency. The vibration of the piezoelectric film 38 is transferred to the vibration film 34. Thus, the vibration film 34 vibrates ultrasonically. As a result, a desired ultrasonic beam is emitted toward a subject (for example, the interior of a human body).

Reflected waves of the ultrasonic waves vibrate the vibration film 34. The ultrasonic vibration of the vibration film 34 ultrasonically vibrates the piezoelectric film 38 at a desired frequency. A voltage is output from the piezoelectric element 35 in accordance with the piezoelectric effect of the piezoelectric film 38. In each element 33, a potential is generated between the top electrode 36 and the bottom electrode 37. The generated potentials are output from the bottom electrode terminals 45 and 47 and the top electrode terminals 44 and 46 as electric signals. The ultrasonic waves are detected in this manner.

Ultrasonic waves are repeatedly transmitted and received. As a result, a linear scan or a sector scan is achieved. When the scan is completed, an image is formed based on digital signals of the output signals. The image thus formed is displayed on the screen of the display panel 15.

If the ultrasonic probe 13 drops onto a floor surface, for example, and an external shock is applied to the housing 16 of the ultrasonic probe 13, a large load acts on the circuit board 24 and the substrate 54. At this time, since the rigid body 27 is in contact with the circuit board 24, the circuit board 24 is kept from deforming. Thus, the stress in the circuit board 24 is dispersed to the rigid body 27, and therefore the circuit board 24 and the substrate 54 can be prevented from being damaged. The shock resistance of the ultrasonic probe 13 can be increased.

According to the present embodiment, at least on the back side of the circuit board 24, the housing 16 has higher stiffness than the circuit board 24. Therefore, even when the rigid body 27 is supported in the housing 16 as described above, the force that is transferred from the circuit board 24 to the rigid body 27 is received by the housing 16. Displacement of the rigid body 27 is relatively avoided. In this manner, the circuit board 24 is reliably kept from deforming. If the stiffness of the housing 16 is insufficient, the circuit board 24 is allowed to deform in accordance with the displacement of the rigid body 27, and it is feared that the circuit board 24 and the substrate 54 may be damaged.

According to the present embodiment, in a plan view as seen in the thickness direction of the circuit board 24, the rigid body 27 is disposed outside the outlines of the connectors 25. Since the connectors 25 are mounted on the circuit board 24, the stiffness of the circuit board 24 is reinforced in those regions that are defined by the outlines of the connectors 25. If the rigid body 27 is disposed outside the outlines of the connectors 25, the stiffness of the circuit board 24 is reinforced also in a region outside the outlines of the connectors 25. Thus, the circuit board 24 is kept from deforming. Furthermore, since the rigid body 27 is disposed so as not to overlap the regions of the connectors 25, the attachment/detachment of the connectors 25 can be ensured even if the rigid body 27 is coupled to the circuit board 24.

According to the present embodiment, on the back side of the elements 33, the elastic bodies 28 are disposed outside the outline of the rigid body 27. Even when the elastic bodies 28 come into contact with the circuit board 24, displacement of the circuit board 24 can be accommodated in accordance with the deformation of the elastic bodies 28. The attachment accuracy required with respect to the substrate is alleviated. At this time, it is preferable that the elastic bodies 28 are sandwiched between the back-side body 22 and the corresponding connectors 25. The elastic bodies 28 press the corresponding connectors 25 against the circuit board 24. As a result, even when a shock is applied to the housing 16 of the ultrasonic probe 13, unintentional detachment of the connectors 25 can be prevented. Furthermore, displacement of the connectors 25 in the height direction is accommodated in accordance with the deformation of the elastic bodies 28, and therefore the positioning accuracy required with respect to the connectors 25 is alleviated.

(5) Configuration of Ultrasonic Probe Aaccording to Second Embodiment

Figure 8:
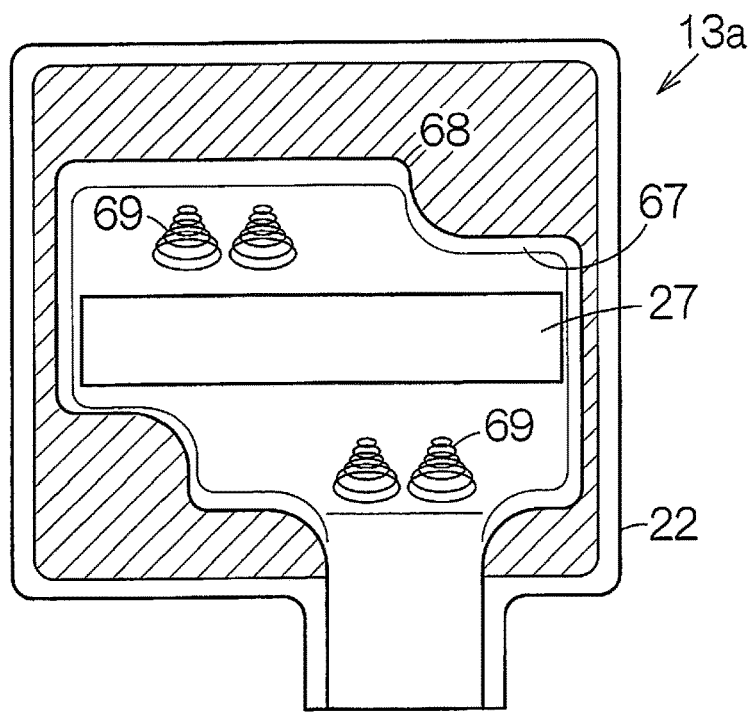
FIG. 8 is an enlarged plan view corresponding to FIG. 7 and schematically showing the structure of a back-side body that is used in an ultrasonic probe according to a second embodiment.

As shown in FIG. 8, in an ultrasonic probe 13a, spring materials 69 can be used as the elastic bodies 28. The spring materials 69 can be formed of helical springs or leaf springs made of metal, for example. The spring materials 69 can be embedded in the back-side body 22 by insert molding during molding of the back-side body 22. These spring materials 69 can function similarly to the above-described elastic bodies 28. The other configurations can be the same as those of the above-described ultrasonic probe 13.

(6) Configuration of Ultrasonic Probe According to Third Embodiment

Figure 9:
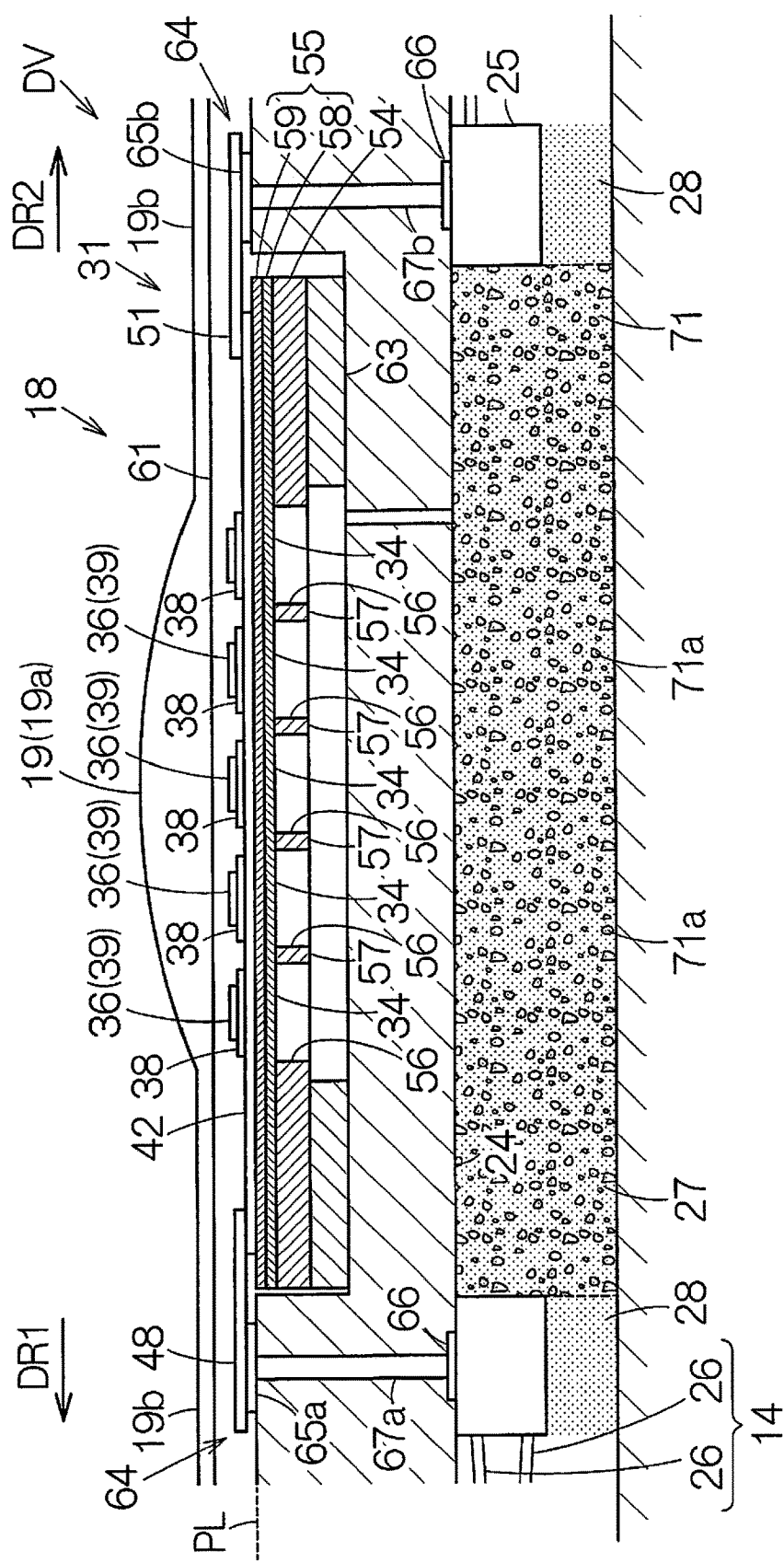
FIG. 9 is an enlarged cross-sectional view corresponding to FIG. 6 and schematically showing the structure of an ultrasonic device unit that is used in an ultrasonic probe according to a third embodiment.

As shown in FIG. 9, in the ultrasonic probe 13, the rigid body 27 and the elastic bodies 28 may be formed of a resin material. Here, the rigid body 27 and the elastic bodies 28 are formed as a single resin body 71. The rigid body 27 and the elastic bodies 28 can be easily processed. Since the rigid body 27 and the elastic bodies 28 are integrated into a single body, the operation of assembling the rigid body 27 and the elastic bodies 28 is simplified.

In the rigid body 27, a filler 71a may be mixed in a base material of the resin material. The stiffness of the rigid body 27 is secured in accordance with the mixing of the filler 71a. In addition, the stiffness of the rigid body 27 and the elasticity of the elastic bodies 28 can be adjusted in accordance with mixing of a filler. The filler 71a can buffer ultrasonic waves that come from the elements 33 to the rear side thereof. Thus, the influence of reflected waves from the resin body 71 toward the elements 33 is avoided.

(7) Configuration of Ultrasonic Probe According to Fourth Embodiment

Figure 10:
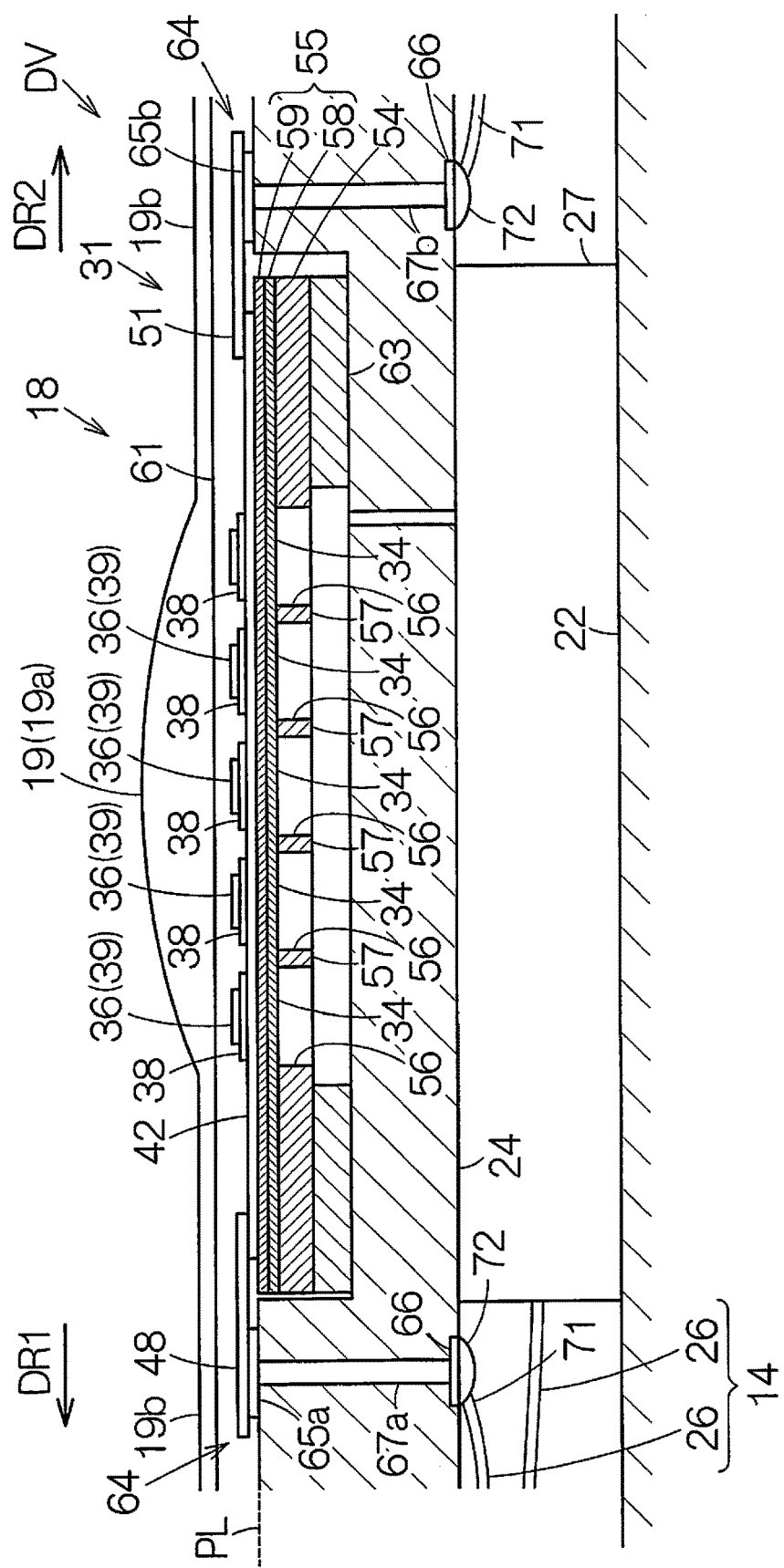
FIG. 10 is an enlarged cross-sectional view corresponding to FIG. 6 and schematically showing the structure of an ultrasonic device unit that is used in an ultrasonic probe according to a fourth embodiment.

As shown in FIG. 10, in the ultrasonic probe 13, the connectors 25 can be omitted and conducting lines 72 of the wires 26 directly joined to the external connection terminals 66. In this case, a soldering material or other joining material 73 is used to join the conducting lines 72, and thus the stiffness of the circuit board 24 is reinforced in those regions containing the external connection terminals 66. If the rigid body 27 is disposed outside the regions containing the external connection terminals 66, the stiffness of the circuit board 24 is reinforced also in a region outside the regions containing the external connection terminals 66. Thus, the circuit board 24 is kept from deforming. The regions containing the external connection terminals 66 can be defined by, for example, rectangles circumscribing the outlines of respective groups of the external connection terminals 66 that are assigned to the individual connectors 25. In addition, in the case where the connectors 25 are omitted, the rigid body 27 may also be in contact with the external connection terminals 66 and the wires 26.

(8) Configuration of Ultrasonic Probe According to Fifth Embodiment

Figure 11:
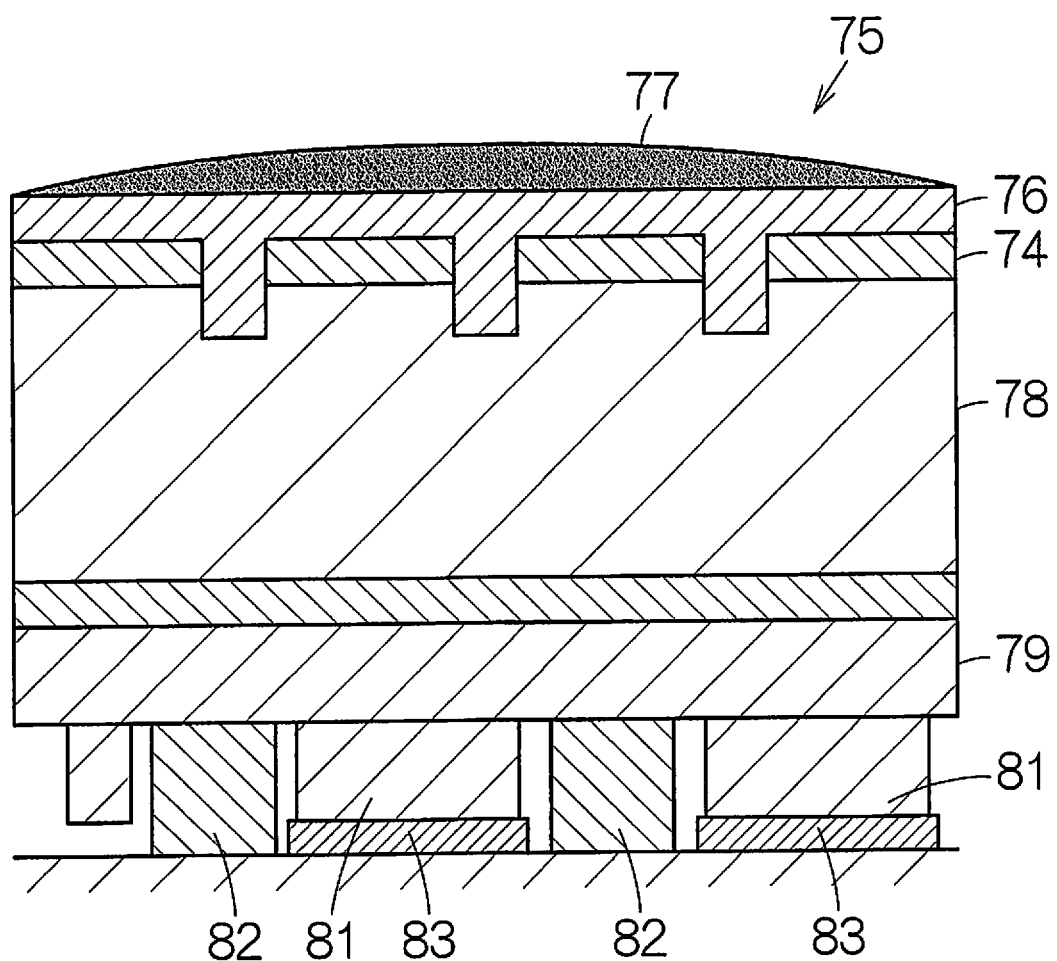
FIG. 11 is an enlarged cross-sectional view schematically showing the structure of an ultrasonic device that is used in an ultrasonic probe according to a fifth embodiment.

As shown in FIG. 11, in the ultrasonic probe 13, the above-described ultrasonic device 18 may be replaced by an ultrasonic device 75 including a bulk element 74. The bulk element 74 has a piezoelectric body sandwiched between a top electrode and a bottom electrode. An acoustic lens 77 is coupled to the bulk element 74 by the function of an acoustic matching layer 76. The bulk element 74 is lined with a backing material 78. A circuit board 79 is connected to the backing material 78. Chip parts and connectors 81 are mounted on the back side of the circuit board 79. In regions around the connectors 81, rigid bodies 82 are in contact with the circuit board 79, and elastic bodies 83 are in contact with the corresponding connectors 81. The other configurations can be the same as those of the above-described ultrasonic probe 13.

Although some embodiments of the invention have been described in detail above, a person skilled in the art will readily understand that various modifications may be made without substantially departing from the novel teachings and the effects of the invention. Therefore, such modifications are entirely included within the scope of the invention. For example, any term described at least once together with a broader or synonymous different term in the specification or the drawings may be replaced by the different term at any place in the specification or the drawings. Moreover, the configurations and operations of the ultrasonic diagnostic apparatus 11, the housing 16, the circuit board 24, the elements 33, and the like are not limited to those described in the foregoing embodiments, but may be modified in various manners.

The entire disclosure of Japanese Patent Application No. 2014-222470 filed on Oct. 31, 2014 is expressly incorporated by reference herein.

What is claimed is:

1. An ultrasonic probe comprising:
a housing that defines an opening and an accommodation space that is continuous with the opening;
an ultrasonic device unit that is disposed in the accommodation space and that has a board including an ultrasonic transducer; and
a rigid body that is in contact with the board and the housing and that has higher stiffness than the board,
in a plan view as seen in a thickness direction of the board, the rigid body being disposed outside an outline of a connector that is mounted on a surface of the board, and the surface being in contact with the rigid body.

2. The ultrasonic probe according to claim 1,
wherein in a plan view as seen in the thickness direction of the board, the rigid body covers a region in which the ultrasonic transducer is disposed.

3. The ultrasonic probe according to claim 1,
wherein in a plan view as seen in the thickness direction of the board, the rigid body is disposed outside a region containing an external connection terminal portion to which a wire is connected on a surface of the board, the surface being in contact with the rigid body.

4. The ultrasonic probe according to claim 1, further comprising:
an elastic body that is disposed on the surface of the board, the surface being in contact with the rigid body, outside an outline of the rigid body in a plan view as seen in the thickness direction of the board and that has a smaller modulus of elasticity than the board.

5. The ultrasonic probe according to claim 4,
wherein the elastic body is sandwiched between the connector and the housing.

6. The ultrasonic probe according to claim 1,
wherein the rigid body and the elastic body are formed of a resin material.

7. The ultrasonic probe according to claim 6,
wherein with respect to the rigid body, a filler is mixed in a base material of the resin material.

8. An electronic apparatus comprising:
the ultrasonic probe according to claim 1; and
a processing unit that is connected to the ultrasonic device unit and that processes an output from the ultrasonic device unit.

9. An ultrasonic imaging apparatus comprising:
the ultrasonic probe according to claim 1;
a processing unit that is connected to the ultrasonic device unit and that processes an output from the ultrasonic device unit and generates an image; and
a display device that displays the image.

* * * * *